US006935185B2

(12) United States Patent
Corleto

(10) Patent No.: US 6,935,185 B2
(45) Date of Patent: Aug. 30, 2005

(54) ACCELERATED METHOD TO DETERMINE OR PREDICT FAILURE TIME IN POLYETHYLENES

(75) Inventor: Carlos Corleto, Seabrook, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 10/737,624

(22) Filed: Dec. 16, 2003

(65) Prior Publication Data

US 2005/0126256 A1 Jun. 16, 2005

(51) Int. Cl.⁷ .......................................... G01N 19/08
(52) U.S. Cl. ...................................................... 73/799
(58) Field of Search .................................. 73/799, 835

(56) References Cited

U.S. PATENT DOCUMENTS

| 3,350,917 | A | * | 11/1967 | Wincklhofer et al. | ......... 374/50 |
| 4,090,489 | A | * | 5/1978 | Barker | ..................... 125/13.01 |
| 5,319,983 | A | | 6/1994 | Brown et al. | ................. 73/799 |
| 5,396,804 | A | * | 3/1995 | Moet et al. | ..................... 73/788 |
| 6,022,933 | A | * | 2/2000 | Wright et al. | ................. 526/68 |
| 6,525,148 | B1 | * | 2/2003 | McDaniel et al. | .......... 526/111 |

OTHER PUBLICATIONS

Brown et al., "A fundamental theory for slow crack growth in polyethylene," 1995, POLYMER, vol. 6, No. 3, ppg 543-548.*
Hu et al., "Correlation of fatigue and creep crack growth in poly(vinyl chloride)", 2003, J. of Mat. Sci, 38, ppg 663-642.*
Dreze et al., "Accelerated Test Methods for Stress Crack Resistance Evaluation of Polyetheylene Pipe Grades" 1998, Solvay Polyolefins Europe, pp. 1-10.*
Web Document, Time Dependent Behavior: Cyclic Loading, 2003, Chapter 9, ppg 9.1-9.12.*
Hu et al., "Effect of impact modification of slow crack growth in poly(vinyl chrloride", 2004, J. Mat. Sci., 39, ppg 2979-2988.*
Lu et al., "Abnormal slow crack growth in polyethylene" 1997, POLYMER, vol. 38, No. 23, ppg 5749-5753.*

(Continued)

*Primary Examiner*—Hezron Williams
*Assistant Examiner*—John Fitzgerald
(74) *Attorney, Agent, or Firm*—Madan, Mossman & Sriram, P.C.

(57) ABSTRACT

An accelerated method of determining the failure time of a polyethylene resin by determining the minimum displacement rate, or the time at minimum displacement rate, using ASTM F 1473-01, then following one of these routes: (1) If failure has not yet occurred, cryogenically fracturing the resin specimen and examining it for slow crack growth to determine whether the anticipated, or desired, failure time is generally before or after the predicted failure time; or (2) Applying the minimum displacement rate, or the time at minimum displacement rate, in the appropriate mathematical formula to predict the failure time for the resin. The mathematical formula is derived from the discovery of a power law relationship between the failure time and minimum displacement rate, or between failure time and the time at minimum displacement rate. Thus, it is not necessary to actually test all the way to failure using ASTM F 1473-01, thereby accelerating testing capability and consequently enabling more rapid development of new resins.

8 Claims, 2 Drawing Sheets

OTHER PUBLICATIONS

Hamouda et al. "Creep damage mechanisms in polyethylene gas pipes" 2001 POLYMER, 42 ppg 5425-5437.*

Plummer et al. "Micromechanisms of slow crack growth in polyethylene under constant tensile load" 2001, POLYMER 42, ppg 9551-9564.*

Singh et al., "Effect of stress ratio and frequency on fatique crack growth rate of 2618 aluminum alloy silicon carbide metal matrix composite" 2001, Bull. Mater. Sci., vol. 24, No. 2, ppg 169-171.*

Parsons et al., "Correlation of stepwise fatique and creep slow crack growth in high density polyethylene" 1999, J. Mat. Sci. 34, ppg 3315-3326.*

Parsons et al., "Correlation of fatique and creep slow crack growth in a medium density polyethylene pipe material" 2000, J. Mat. Sci. 35, ppg 2659-2674.*

ASTM International, Designation: F 1474—98 (Reapproved 2001), *Standard Test Method for Slow Crack Growth Resistance of Notched Polyethylene Plastic Pipe*, pp. 1166-1168, 3 Figs.

ASTM International, Designation: F 1473—01, *Standard Test Method for Notch Tensile Test to Measure the Resistance to Slow Crack Growth of Polyethylene Pipes and Resins*, pp. 1160-1165, 3 Figs, 1 Table.

ASTM International, Designation: D 2837—01, *Standard Test Method for Obtaining Hydrostatic Design Basis for Thermoplastic Pipe Materials*, pp. 281-294, 5 Tables.

ASTM International, Designation: D 1598—97, *Standard Test Method for Time-to-Failure of Plastic Pipe Under Constant Internal Pressure*, pp. 24-27.

ASTM International, Designation: F 3417—99, *Standard Test Method for Enthalpies of Fusion and Crystallization of Polymers by Differential Scanning Calorimetry (DSC)*, 330-333, 2 Figs.

* cited by examiner

ACCELERATED METHOD TO DETERMINE OR PREDICT FAILURE TIME IN POLYETHYLENES

BACKGROUND OF THE INVENTION

1. Field of the Invention

The present invention relates to methods of determining time to failure in resins. More particularly, it relates to an accelerated method of determining time to failure of polyethylene resins frequently used in pipe applications.

2. Background of the Art

High resistance to slow crack growth is one of the most important physical properties sought for resins to be used under a variety of conditions, and particularly those that will be used in applications such as pipelines where pressurization can result in dangerous and costly failures. Slow crack growth, which is the slow extension of a crack with time, can significantly reduce the life expectancy of such pipelines, and accurate means of measuring, and therefore predicting, the point of failure are necessary to enable appropriate replacement scheduling.

As used herein, failure refers to brittle failure, which is splitting of a test specimen, or bursting, splitting, or weeping, i.e., seepage of liquid, occurring in an actual pipe or in a pipe specimen, without visible permanent material deformation such as stretching, elongation, or necking down occurring in the area of the break. However, the resin industry has been handicapped in developing and testing new resins for such applications because of the long time periods required to test these materials using many currently-employed methods.

Generally, there are two types of test methods currently being employed. One type involves actually preparing a pipe of the resin and pressurizing it under applicable conditions until failure occurs. These tests are exemplified by methods such as those described by the American Society for Testing Materials (ASTM) in its tests designated as F1474 (also called ISO 13479); ASTM D2837; and ASTM D1598. While these tests are often necessary for actual resin certification, they are expensive and time-consuming, and thus, their use in conjunction with resin development tends to slow down development of new resins. Simply stated, development of new resins is not generally initiated until testing shows that already-developed resins are unsatisfactory, so shortened testing time enables more rapid initiation of development of new resins.

The other type of tests are laboratory scale tests. These include the frequently-used ASTM F1473, also called the Pennsylvania Notched Test, or "PENT," and the Full-Notched Creep Test, also called "FNCT," both of which provide faster and more economical ways to assess slow crack growth in resins. However, even these tests present increasingly significant impediments to resin development, as new resins with improved performance exhibit ever-greater resistance to slow crack growth, and therefore extend the time required to accomplish testing.

SUMMARY OF THE INVENTION

The present invention provides an accelerated method for determining or predicting failure time in polyethylene materials. It is a laboratory scale test including many of the parameters of ASTM F 1473-01, the so-called "PENT", but it differs from that test in that it continues only until either actual failure or the Min $\delta_R$, i.e., minimum displacement rate, and its time of occurrence—whichever occurs first—is obtained. If the specimen has not failed prior to that time, there are then two routes which can be taken: (1) the specimen is cryogenically fractured and examined to determine if slow crack growth has occurred, from which it can be determined that, if slow crack growth has occurred, PENT failure time is before an anticipated or desired failure time, and if slow crack growth has not occurred, PENT failure time is after the anticipated or desired failure time; or (2) the Min $\delta_R$ or time at Min $\delta_R$ can be used to predict PENT failure time by using it, as appropriate, in one of the following formulas:

$$\text{Failure Time}=0.2667(\text{Min }\delta_R)^{-0.9401} \qquad \text{[Formula 1]}$$

wherein R is 0.9916; and $$\text{Failure Time}=3.8272 \text{ (time at Min }\delta_R)^{1.0348} \qquad \text{[Formula 2]}$$

wherein R is 0.9805.

Since most of the time in the PENT involves slow crack growth propagation which eventually results in failure, subsequent to determining the Min $\delta_R$, the accelerated method of the present invention dramatically reduces the time required to determine or predict the failure point.

DETAILED DESCRIPTION OF THE EMBODIMENTS

Figure 1:
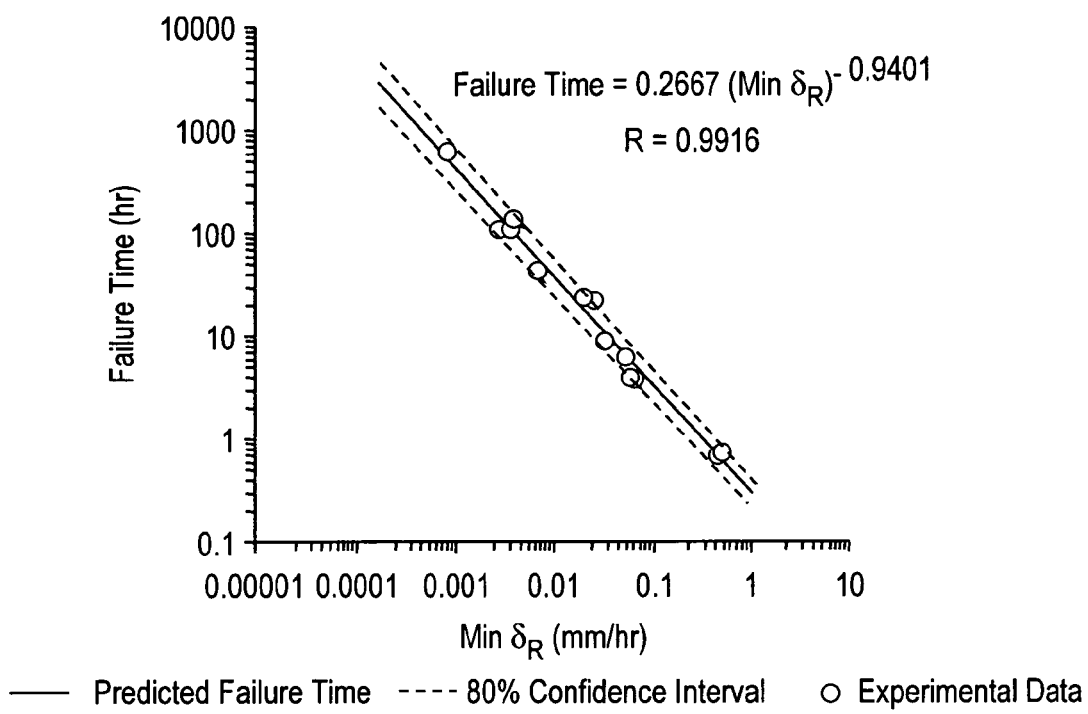
FIG. 1 is a graph showing Failure Time plotted against Min $\delta_R$ for thirteen tests of six different polyethylene resins.

The present novel method enables acceleration, i.e., decrease, in the amount of time necessary to determine failure rate, when compared with the traditional PENT, by as much as 3.6 to 4.6 times. This acceleration is due to the fact that it is not generally necessary to test all the way to failure to predict PENT performance. This improved and highly useful method can be carried out as follows.

Specimen preparation and apparatus as described in ASTM F 1473-01 are employed. ASTM F 1473-01 is incorporated herein by reference in its entirety. The present invention therefore anticipates following, for example, the general instructions of the designated ASTM test devoted to preparing the compression molded plaques of the polyethylene material to be tested; cutting the specimen from the plaque and notching the specimen as described in section 8.5 thereof; conditioning the plaque (or the specimen) at least 1 hour at the test temperature; and calculating and applying the appropriate test load according to the relationship:

a. $P = \sigma \times w \times t$, in which P is the test load, σ is the stress, w is the specimen width, and t is the specimen thickness, with the variables w and t being based on the unnotched cross section. If σ is in the units of megapascals and w and t are in millimeters, then P is in Newtons.

The important distinction in the present invention is that, while testing according to ASTM F 1473-01 is carried out to the point of failure, which in the case of some recently-developed resins can be several thousand hours, testing in the present invention generally requires much less time.

"Failure" as used in the designated test procedure is when the two halves of the specimen separate completely, or when extensive deformation occurs In the remaining ligament. In sharp contrast with ASTM F 1473-01, the present invention carries out the procedure only until a Min $\delta_R$ is reached. Min $\delta_R$ refers to a minimum displacement rate, which is the point at which the crack growth, due to craze breakdown, is initiated at the tip of the notch, and thus occurs well before actual failure. This event can be related to what some researchers have called crack tip opening displacement ("CTOD"), although there is probably a difference in that CTOD refers to only the viscoplastic molecular disentanglement process in the craze zone ahead of the crack tip prior to the onset of slow crack growth, whereas the Min $\delta_R$ further includes any viscoelastic deformations occurring throughout the specimen. Min $\delta_R$ is measured In millimeters per hour.

It is an interesting fact, and important to the present invention, that even though failure times are different for each resin, each polyethylene material resin shows an equivalent deceleration of its displacement rate until its unique Min $\delta_R$ is reached, followed by rapid acceleration to its point of failure. Because the decelerations are approximately equivalent, a relationship between Min $\delta_R$ and failure time has now been discovered, and can be applied to any polyethylene material resin, regardless of molecular architecture, e.g., homopolymer and hexene- and butene-based copolymers, or molecular distribution, e.g., bimodal and unimodal, and at any given testing temperature, to predict its failure time. That relationship is essentially a power law and can be mathematically represented by the following formulas:

Failure Time=0.2667(Min $\delta_R$)$^{-0.9401}$ [Formula 1]

wherein R is 0.9916, and

Failure Time=3.8272 (time at Min $\delta_R$)$^{1.0348}$ [Formula 2]

wherein R is 0.9878. R is the value for the linear regression analysis of the data points.

These mathematical formulas were developed based on two "master graphs" prepared using a wide variety of polyethylene resins, of various architectures and molecular distributions, which illustrated the fact that the decelerations to Min $\delta_R$ appear to be common to all of the resins of the polyethylene family. These master graphs are included herein as FIGS. 1 and 2 and their development is further discussed in Examples 1 and 2.

The present invention is amenable to use of either instrumented or non-instrumented apparatuses. In general a non-instrumented apparatus is capable of determining the Min $\delta_R$ and therefore also the time at Min $\delta_R$. An apparatus suitable for carrying out the testing is described in the designated ASTM F 1473-01 section. Other apparatuses suitable for this purpose, which can be used within the scope of the present invention, include, for example, that described in U.S. Pat. No. 5,319,983, which purports to also enable notching without any significant residual stresses forming ahead of the notch.

Thus, such an apparatus can be successfully used where an anticipated or desired failure time can be selected and where the individual carrying out the testing is ready, if necessary, to perform further cryogenic fracturing if failure is not reached prior to, or concurrent with, the Min $\delta_R$. In this case, the specimen can be cryogenically fractured by any means known to those skilled in the art, such as, for example, immersion in liquid nitrogen for at least 5 minutes. Following this immersion, it is advantageous to break the specimen along the initial crack plane and then observe the fracture surfaces to determine whether or not slow crack growth has occurred during the testing. This might require using an optical microscope to facilitate detection of very small amounts of such crack growth.

It is important to ensure that slow crack growth is not confused with plastic zone and cryogenic crack growth. Determination of whether such slow crack growth has occurred is key to predicting PENT failure time, since if such is detected, PENT failure time is obviously greater than time at Min $\delta_R$ but less than the anticipated or desired failure time. If such slow crack growth is not detected, PENT failure time is greater than anticipated or desired failure time.

Figure 2:
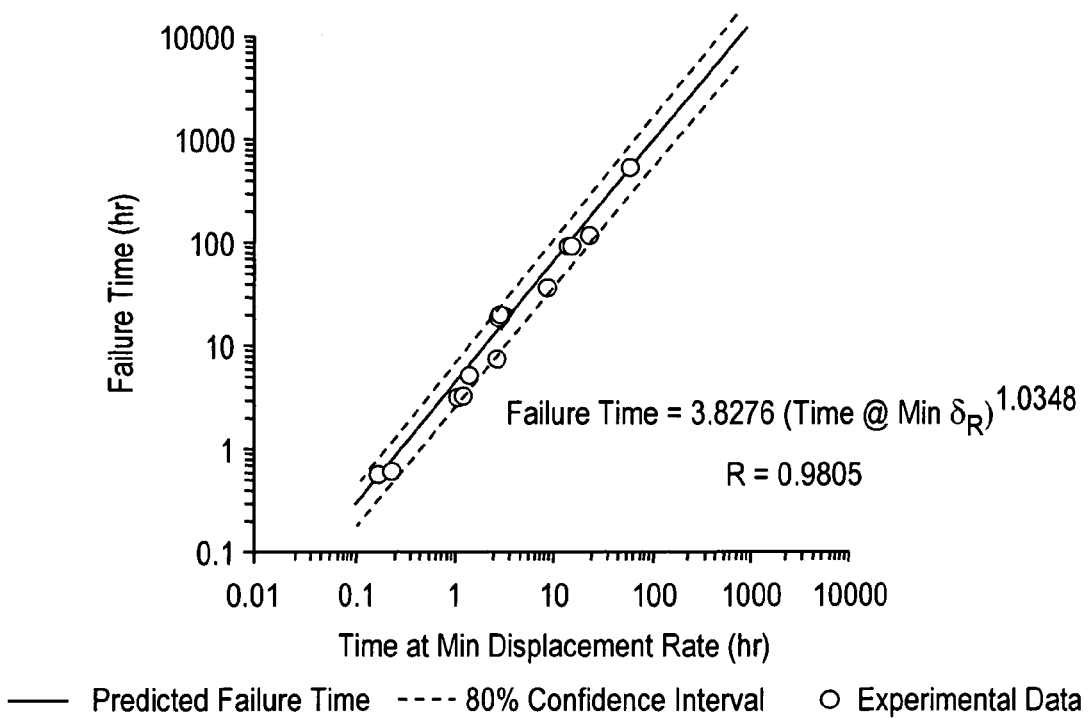
FIG. 2 is a graph showing Failure Time plotted against time at Min $\delta_R$ for the same thirteen tests of six polyethylene resins.
Figure 3:
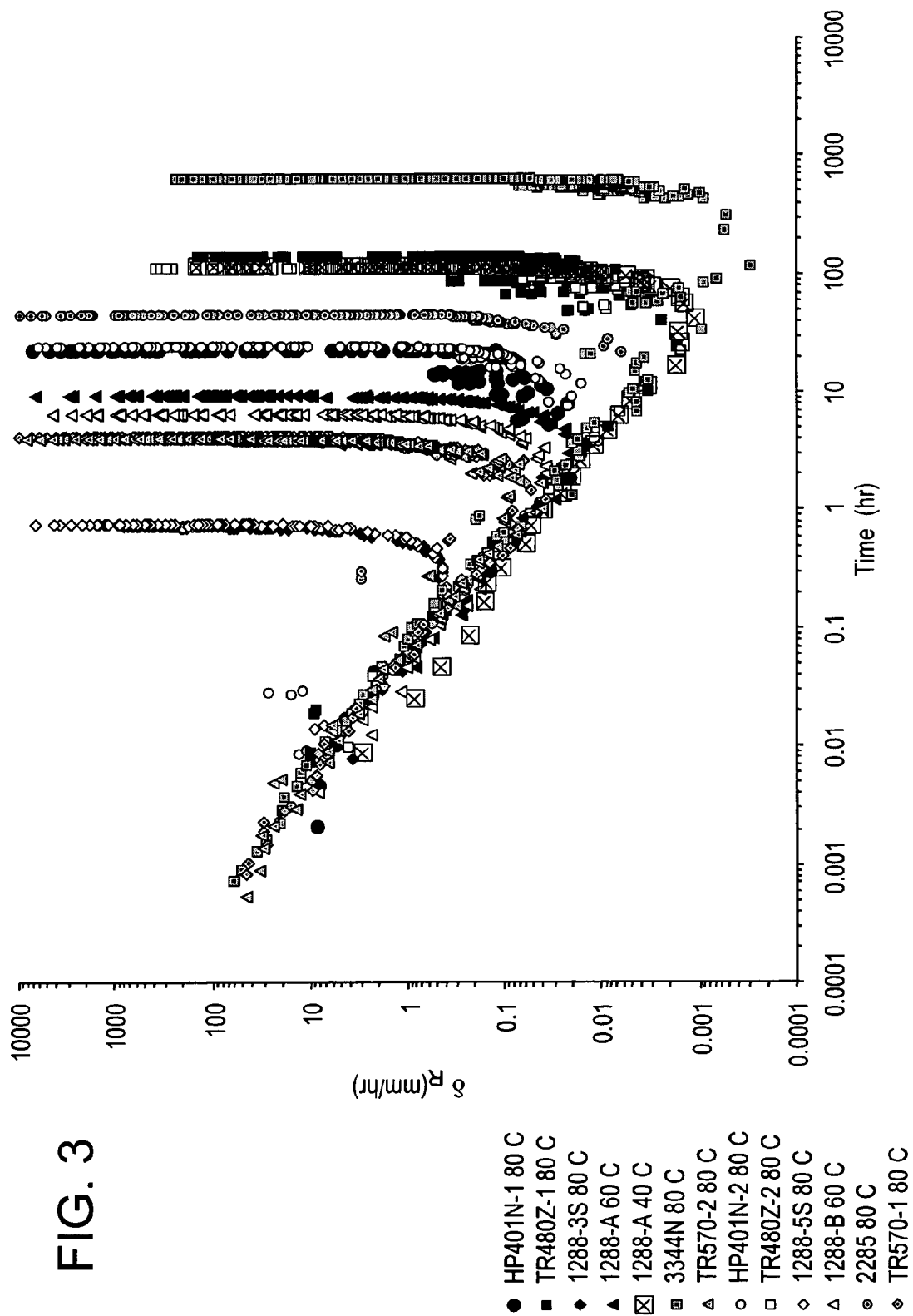
FIG. 3 is a graph showing $\delta_R$ plotted against time for the same thirteen tests of six polyethylene resins.

An instrumented apparatus provides an even faster and more efficient means of determining the $\delta_R$ by calculating and plotting it versus test time on a computer monitor to clearly detect when the Min $\delta_R$ is reached. It is desirable to continue testing just past this point to ensure that a true minimum has been reached. From this point it is simple to plug this information, as either Min $\delta_R$ or time at Min $\delta_R$, into one of the two formulas, i.e., Formula 1 or Formula 2, as appropriate, to mathematically calculate the predicted failure time (PFT). Since the inventors hereof have determined that a confidence level of about 80% is achieved by this PFT, based on observed failure time data scatter, it is advisable to calculate upper and lower PFT's using 80% confidence intervals. High R-values at this point strongly confirm these relationships. This data scatter may be attributable to the displacement noise level of the instrument used to measure displacement versus time. The potential data scatter can also be depicted graphically, as shown in FIGS. 1 and 2, and used to bracket predicted failure time with close to 100% confidence.

The following examples are provided to illustrate the present invention and are not intended to be, nor should they be construed as being, limitative thereof in any way.

EXAMPLE 1

Minimum displacement rates (Min $\delta_R$) are obtained for thirteen tests of six different resins following the procedures outlined in ASTM F 1473-01, except that the resins are tested at different temperatures ranging from 40° C. to 80° C. These rates were plotted on a graph showing Failure Time in hours against Min $\delta_R$ in millimeters per hour. The results are shown in FIG. 1. This forms one of the "master graphs."

EXAMPLE 2

The time at Minimum displacement rate (Min $\delta_R$) is obtained for the same thirteen tests of six different resins as tested in Example 1. This data is plotted, in hours, against Failure Time in hours. The results are shown in FIG. 2. This forms the second "master graph."

EXAMPLE 3

Testing for $\delta_R$ is carried out on the same thirteen resins used in the previous examples. The results are plotted on a graph showing $\delta_R$ in millimeters per hour against time in hours. Although the specimens are tested at different temperatures as indicated, ranging from 40° C. to 80° C., it will be seen that all specimens show an essentially identical deceleration to Min $\delta_R$, followed by an acceleration toward or to failure that presents on the graph as an essentially vertical line. It is thus the time at which minimum displacement rate is achieved that is then plotted on FIG. 1 and FIG. 2 to enable extrapolation to Formula 1 and Formula 2, enabling an easy and convenient means to predict Failure Time for other resins.

In the foregoing specification, the invention has been described with reference to specific embodiments thereof, and has been demonstrated as effective in determining, either by observation or prediction, a failure time for a given polyethylene material resin. However, it will be evident that various modifications and changes can be made to the steps and components used in the method without departing from the broader spirit or scope of the invention as set forth in the appended claims. Accordingly, the specification is to be regarded in an illustrative rather than a restrictive sense. For example, specific types of apparatuses and means of measurement, falling within the claimed parameters, but not specifically identified or tried in the present invention's method, are anticipated and expected to be within the scope of this invention.

What is claimed is:

1. An accelerated method of determining or predicting failure time in polyethylene materials, comprising selecting an anticipated or desired failure time for a polyethylene material specimen; conducting a PENT (Pennsylvania Notched Test) on the specimen according to ASTM F1473-01 for a time equivalent to the time at Min $\delta_R$, wherein Min $\delta_R$=minimum displacement rate in millimeters and time is measured in hours, that corresponds to the anticipated or desired failure time; and either determining that, (a) if failure has occurred, PENT failure time is before the anticipated or desired failure time, and (b) if failure has not occurred, cryogenically fracturing the specimen to determine whether slow crack growth has occurred, such that (i) if slow crack growth has occurred, PENT failure time is greater than time at Min $\delta_R$ but less than anticipated or desired failure time, and (ii) if slow crack growth has not occurred, PENT failure time is greater than anticipated or desired failure time; or predicting PENT failure time by using either Min $\delta_R$ or time at Min $\delta_R$, as appropriate, in one of the following formulas:

$$\text{Failure Time}=0.2667(\text{Min } \delta_R)^{-0.9401} \quad \text{[Formula 1]}$$

wherein R is 0.9916; and $$\text{Failure Time}=3.8272 \text{ (time at Min } \delta_R)^{1.0348} \quad \text{[Formula 2]}$$

wherein R is 0.9805.

2. The method of claim 1 wherein the PENT is carried out at a stress of 4 megapascals.

3. The method of claim 1 wherein cryogenic fracturing is carried out by immersion of the specimen in liquid nitrogen followed by breaking the specimen along the initial crack plane.

4. The method of claim 1 wherein Min $\delta_R$ or time at Min $\delta_R$ are determined using a non-instrumented or instrumented apparatus.

5. The method of claim 1 wherein the polyethylene material is selected from the group consisting of homopolymers and hexene- and butene-based copolymers.

6. The method of claim 2 wherein the homopolymers and copolymers are bimodal or unimodal.

7. An accelerated method of determining or predicting failure time in polyethylene materials, comprising selecting an anticipated or desired failure time for a polyethylene material specimen; conducting a PENT (Pennsylvania Notched Test) on the specimen according to ASTM F1473-01 for a time equivalent to the time at Min $\delta_R$, wherein Min $\delta_R$=minimum displacement rate in millimeters and time is measured in hours, that corresponds to the anticipated or desired failure time; and determining that, (a) if failure has occurred, PENT failure time is before the anticipated or desired failure time, and (b) if failure has not occurred, cryogenically fracturing the specimen to determine whether slow crack growth has occurred, such that (i) if slow crack growth has occurred, PENT failure time is greater than time at Min $\delta_R$ but less than anticipated or desired failure time, and (ii) if slow crack growth has not occurred, PENT failure time is greater than anticipated or desired failure time.

8. An accelerated method of determining or predicting failure time in polyethylene materials, comprising selecting an anticipated or desired failure time for a polyethylene material specimen; conducting a PENT (Pennsylvania Notched Test) on the specimen according to ASTM F1473-01 for a time equivalent to the time at Min $\delta_R$, wherein Min $\delta_R$=minimum displacement rate in millimeters and time is measured in hours, that corresponds to the anticipated or desired failure time; and predicting PENT failure time by using either Min $\delta_R$ or time at Min $\delta_R$, as appropriate, in one of the following formulas:

$$\text{Failure Time}=0.2667(\text{Min } \delta_R)^{-0.9401} \quad \text{[Formula 1]}$$

wherein R is 0.9916; and $$\text{Failure Time}=3.8272 \text{ (time at Min } \delta_R)^{1.0348} \quad \text{[Formula 2]}$$

wherein R is 0.9805.

* * * * *